United States Patent [19]

Knifton

[11] 4,270,015
[45] May 26, 1981

[54] MANUFACTURE OF ETHYLENE FROM SYNTHESIS GAS (D#75,673-C1)

[75] Inventor: John F. Knifton, Austin, Tex.

[73] Assignee: Texaco Inc., White Plains, N.Y.

[21] Appl. No.: 167,875

[22] Filed: Jul. 14, 1980

Related U.S. Application Data

[63] Continuation-in-part of Ser. No. 8,988, Feb. 5, 1979, abandoned.

[51] Int. Cl.³ .............................................. C07C 1/00
[52] U.S. Cl. .................... 585/324; 585/639;
560/227; 560/263; 560/265; 560/230;
260/410.6; 260/410.9 R; 560/1; 560/8; 560/19;
560/47; 560/122; 560/190; 560/226; 546/318;
546/321
[58] Field of Search ...................... 585/639, 650, 324;
560/263, 265, 227, 230

[56] References Cited

U.S. PATENT DOCUMENTS 2,549,470  4/1951  Howk et al. ..................... 568/902

OTHER PUBLICATIONS

Blades, Can. J. Chem., 32 pp. 366-372, 1954.
De Puy et al., Chem. Rev. 60, pp. 431-433, 1960.

Primary Examiner—Howard T. Mars
Attorney, Agent, or Firm—Carl G. Ries; Robert A. Kulason; Bernard Marlowe

[57] ABSTRACT

This invention concerns a two-step process for the preparation of ethylene from mixture of carbon monoxide and hydrogen (commonly known as synthesis gas) by reaction of said carbon monoxide/hydrogen mixtures with a carboxylic acid in the presence of one or more ruthenium catalyst complexes to form an ethyl ester of said carboxylic acid coreactant, followed by pyrolysis of said ethyl ester intermediate to ethylene.

12 Claims, No Drawings

MANUFACTURE OF ETHYLENE FROM SYNTHESIS GAS (D#75,673-C1)

SUMMARY AND BACKGROUND OF INVENTION

This invention is a continuation-in-part of Ser. No. 8988 filed Feb. 5, 1979 now abandoned and concerns a two-step process for the preparation of ethylene from mixtures of carbon monoxide and hydrogen (commonly known as synthesis gas or syngas).

More specifically, the inventive process concerns the selective synthesis of ethylene from synthesis gas by reacting said mixtures of $CO/H_2$ with one or more carboxylic acid coreactants in the presence of one or more ruthenium catalyst complexes to form ethyl esters of said carboxylic acid coreactants, and then pyrolyzing said ethyl ester intermediates to ethylene. The process is exemplified by but not limited to CO hydrogenation in the presence of an acyclic carboxylic acid (RCOOH where R is an organic radical) to form an ethyl ester of said acid, which upon pyrolysis yields ethylene and regenerates said acid according to stoichiometry of eq (1) and (2)

$$2CO + 4H_2 + RCOOH \rightarrow C_2H_5OOCR + 2H_2O \quad (1)$$

$$C_2H_5OOCR \rightarrow C_2H_4 + HOOCR \quad (2)$$

Alternatively, the ethyl ester may be isolated and used, as is, or as an intermediate in the production of other useful and important chemicals. For example, ethyl esters such as ethyl acetate and ethyl propionate are widely used as solvents, particularly for surface coatings. Alternatively, the ethyl ester ($RCOOC_2H_5$) may be hydrolyzed to ethanol as illustrated in eq 3, and the ethanol used as a source of other two carbon molecules of commercial importance, and their derivatives, such as acetaldehyde, acetic acid, acetic anhydride, acetaldol, and cellulose acetates.

$$RCOOC_2H_5 + H_2O \rightarrow RCOOH + C_2H_5OH \quad (3)$$

It is the purpose of this invention to provide a new, two-step route to the production of ethylene using mixtures of carbon monoxide and hydrogen as the primary building block, that proceeds via the intermediate formation of ethyl esters of carboxylic acids.

A number of routes have been suggested previously for the production of ethylene from synthesis gas*, including:

Variations in Fischer-Tropsch technology
Methanol homologation to ethanol, followed by dehydration
Dimethyl ether cracking
Direct synthesis from $CO/H_2$ mixtures over alkaline iron oxide catalysts

*P. H. Spitz, Chemtech, May 1977, p. 295

The prior art discloses a number of references to the use of ruthenium catalysts for the generation of alcohols or esters of carboxylic acids. These references all contain deficiencies which the present application overcomes.

In Gresham (U.S. Pat. No. 2,632,014) ruthenium is used as a catalyst to convert carbon monoxide and hydrogen into a variety of products. The ruthenium catalyst as the dioxide was dispersed in an aqueous solution. The product distribution from the reaction was dependent upon the pH of the aqueous reaction medium. The product composition varied from 12% $C_2$ to $C_{10}$ alcohols and 88% wax in a 0.33 molal $H_3PO_4$ solution to 91% $C_2$ to $C_{10}$ alcohols and 9% wax in a 0.5 molal $KHCO_3$ solution. The process of Gresham gives a wide distribution of products. The total of all the alcohols with carbon numbers from 2 to 10 varied from 12 to 91%.

While Gresham shows the formation of alcohols, it is well known that the formation of esters in the presence of molar excesses of water and either a basic or acidic catalyst would be minimized or precluded.

Walker et al (U.S. Pat. No. 3,878,290) describe the preparation of divalent metal salts of dodecarhodiumtriconta carbonyls. Ruthenium is only mentioned in the specification and no examples employing ruthenium are given. Moreover, the reaction of carbon monoxide and hydrogen in the presence of this catalyst leads to a diverse spectrum of oxygenates. While data are not set forth on the yields of oxygenates in this patent, the numerous classes of oxygenates would preclude any specificity for the formation of $C_2$ alcohols.

Howk et al (U S. Pat. No. 2,549,470) show techniques to produce a distribution of high molecular weight alcohols or esters with little specificity towards the $C_2$ alcohols or esters. The low molecular weight alcohols or esters produced by the disclosed techniques are present in about 10% yields.

Alderson et al (U.S. Pat. No. 3,040,090) are concerned with the reaction of ethylenic compounds with CO and a lower alcohol or water to obtain a spectrum of oxygenates.

Gresham et al (U.S. Pat. No. 2,534,018) teach the use of a cobalt fluoride catalyst in the presence of carbon monoxide and hydrogen to form polyhydric alcohols and esters. This patent does not teach the formation of ethyl esters in high yields and with high conversions of CO and $H_2$.

Cawse (U.S. Pat. No. 4,013,700) teaches the use of rhodium complexes to produce polyhydric alcohols, ethers or esters. Also formed in the reaction mixtures are small quantities of monohydric alcohols containing less than 1% ethanol (example 1).

The prior art cited above can be characterized as deficient in anticipating the invention of this application because nowhere therein is any reacting of the conversion of carbon monoxide and hydrogen to ethyl esters of lower aliphatic carboxylic acids in high yields and at high conversions.

To our knowledge, however, the production of ethylene from synthesis gas via the intermediate formation of ethyl esters (eq 1 and 2) has not been proposed previously. This new route to ethylene has several distinct and important advantages, most notably, both the initial formation of the ethyl esters from syngas, using the novel class of ruthenium catalysts disclosed herein, and the subsequent pyrolysis of said ethyl esters, selective chemical reactions when carried out in accordance with the examples and the accompanying specification. In particular, the use of the ruthenium catalysts disclosed herein represent an important advance in the technology for making two-carbon molecules and their derivatives, directly from synthesis gas.

The selective pyrolysis of esters, particularly acyclic esters, to alkenes and the corresponding acids, is well documented in the literature. The reaction may be carried out in either the liquid or vapor phases. It does not require a catalyst and is relatively simple in experimental procedure. Furthermore, yields of alkene elimination product are nearly always excellent and sometimes quantitative. Themolysis of ethyl esters of aliphatic carboxylic acids, for example, has been reported to yield ethylene and the corresponding carboxylic acids in a number of cases[*]. Specific examples include the pyrolysis of ethyl acetate to ethylene and acetic acid[****] (eq 2).

[**]See: C. H. DePuy and R. W. King, Chemical Reviews, 60, 431 (1960).
[*]See: G. G. Smith and F. W. Kelly, Progress in Physical Organic Chemistry, Vol. 8, Wiley-Interscience (1971) [**]A. T. Blades, Can. J. Chem., 32, 366 (1954).

PROCESS EMBODIMENTS

In our aspect of this invention, ethylene is prepared from mixtures of carbon monoxide and hydrogen (synthesis gas) by first reacting said mixtures with a carboxylic acid coreactant in the presence of one or more ruthenium catalyst complexes to form an ethyl ester of said carboxylic acid coreactant, followed by pyrolysis of said ethyl ester intermediate to ethylene.

In another practice of this invention, ethylene is prepared from a synthesis gas mixture of carbon monoxide and hydrogen by a process comprising the following:

(a) Contacting the mixture of carbon monoxide and hydrogen with a liquid medium containing an aliphatic carboxylic acid or acid anhydride and a ruthenium-Group VA ligand catalyst complex.

(b) Heating the reaction mixture to temperatures of between about 100° and 350° C., at superatmospheric pressures of 500 psi or greater with sufficient carbon monoxide and hydrogen to satisfy the stoichiometry of the desired ester synthesis, until substantial formation of the desired ethyl esters has been achieved.

(c) Isolating said ethyl esters contained therein, and pyrolyzing said esters under an inert atmosphere to yield the desired ethylene and regenerating the coreactant carboxylic acid.

In order to present the inventive concept in the greatest possible detail as to promote its understanding, the following supplementary disclosure is submitted:

SYNTHESIS OF ETHYL ESTERS

A. Ruthenium Catalyst Composition

Catalyst precursors that are suitable in the practice of the first stage of this invention, particularly the synthesis of ethyl esters from synthesis gas, contain ruthenium. The most effective catalysis is achieved when the ruthenium species are solubilized in the carboxylic acid coreactant employed to satisfy the stoichiometry of eq. 1.

The preferred ruthenium portion of the catalyst may take many different forms. For instance, the ruthenium may be added to the reaction mixture in an oxide form, as in the case, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, anhydrous ruthenium(III) chloride and ruthenium nitrate, or as the salt of a suitable organic carboxylic acid (see Section B, below), for example, ruthenium(III) acetate, ruthenium(III) propionate, ruthenium octanoate, ruthenium napthenate, ruthenium valerate and ruthenium(III) acetylacetonate. The ruthenium may also be added to the reaction zone as a carbonyl or hydrocarbonyl derivative. Here, suitable examples include triruthenium dodecacarbonyl, hydrocarbonyls such as $H_2Ru_4(CO)_{13}$ and $H_4Ru_4(CO)_{12}$, and substituted carbonyl species such as the tricarbonylruthenium(II) chloride dimer $[Ru(CO)_3C_{12}]_2$.

The other important component of the catalyst is one or more Group VA tertiary donor ligands. The key elements of the Group VA ligands include nitrogen, phosphorous, arsenic and antimony. These elements, in their trivalent oxidatin states, particularly tertiary phosphorous and nitrogen, may be bonded to one or more alkyl, cycloalkyl, aryl, substituted aryl, aryloxide, alkoxide and mixed alkaryl radicals, each containing from 1 to 12 carbon atoms, or they may be part of a heterocyclic ring system, or be mixtures thereof. Illustrative examples of suitable ligands that may be used in this invention include: triphenylphosphine, tri-n-butylphosphine, triphenylphosphite, triethylphosphite, trimethylphosphite, trimethylphosphine, triethylphosphine, trimethylarsine, triphenylarsine, tri-p-tolphosphine, tricyclohexylphosphine, dimethylphenylphosphine, trioctylphosphine, tri-o-tolylphosphine, 1,2-bis (diphenylphosphine)ethane, triphenylstilbine, trimethylamine, triethylamine, tripropylamine, tri-n-octylamine, pyridine, 2,2'-dipyridyl, 1,10-phenanthroline, quinoline, N,N'dimethylpiperazine, 1,8-bis(dimethylamino) naphthalene and N,N-dimethylaniline.

One or more of these ruthenium-tertiary Group VA donor ligand combinations may be preformed, prior to addition to the reaction zone, as in the case, for example, of tris(triphenylphosphine)ruthenium(II) chloride and dicarbonylbis(triphenylphosphine)ruthenium(II) chloride or alternatively, said complexes may be formed in situ.

The performance of each of these classes of ruthenium Group VA ligand catalyst is illustrated by the accompanying examples, described below.

A further important class of ruthenium catalyst precursor, useful in the conversion of carbon monoxide hydrogen mixtures to ethyl ester derivatives, consists of one or more suitable ruthenium oxide, salt and/or carbonyl derivative species in combination with a cocatalyst. There are several classes of suitable co-catalysts. One such class which may be added to the reaction mixtures to enhance the activity of the solubilized ruthenium catalysts is the salts of the alkali and alkaline earth metals. Illustrative examples of effective alkali metal salts include the alkali metal halides, for instance, the fluoride, chloride, bromide and iodide salts, together with the alkali and alkaline earth metal salts of suitable carboxylic acids (see Section B, below). The preferred alkali and alkaline earth metal salts are the bromides. These salts may be added over a wide range of concentrations, from about 0.01 to at least 102 moles of alkali or alkaline earth salt per gm atom of ruthenium present in the reaction mixture.

Salts of quaternary ammonium and phosphonium cations are also effective as cocatalysts in the process of this invention. Suitable quaternary phosphonium salts are those which are substantially inert under the CO-hydrogenation conditions and which have the formula:

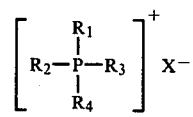

where $R_1$, $R_2$, $R_3$ and $R_4$ are organic radicals bonded to the phosphorous atom by a saturated aliphatic carbon atom, and X is an anionic species, preferably a halogen ion such as bromide. The organic radicals useful in this instance include alkyl, aryl, alkylaryl and cycloalkyl radicals having, where possible, 1 to 20 carbon atoms. The alkyl radicals may contain both branched and linear chains and include the methyl, ethyl, n-butyl, isobutyl, heptyl, 2-ethylhexyl, and dodecyl radicals. Suitable aryl and alkylaryl radicals include, but are not limited to, phenyl, p-methacrylphenyl, benzyl, p-tolyl, p-alkylphenyl, o-tolyl and m-tolyl. Suitable quaternary phosphonium salts useful in the practice of this invention include tetramethylphosphonium bromide, tetrabutylphosphonium chloride, tetrabutylphosphonium iodide, tetrabutylphosphonium bromide, tetraphenylphosphonium bromide, heptyl(triphenyl)phosphonium bromide and methyl(triphenyl)phosphonium bromide. The corresponding quaternary phosphonium hydroxides, nitrates and carboxylic acid salts may also be useful in this instance, as well as the corresponding quaternary ammonium salts such as tetramethylammonium bromide and tetra-n-propylammonium bromide, and the corresponding iminium salts such as bis(triphenylphosphine)iminium nitrate. Examples 1–8 provide evidence for the effectiveness of the ruthenium oxide-quaternary phosphonium and ammonium couples.

B. Carboxylic Acids

Carboxylic acids useful in the process of this invention form the acid moiety of the desired ethyl ester intermediate. Preferably, said acids are also useful as solvents for the ruthenium catalyst combinations. Suitable carboxylic acids include aliphatic acids, alicyclic monocarboxylic acids, heterocyclic acids and aromatic acids, both substituted and non-substituted. For example, this invention contemplates the use of lower mono aliphatic acids of 1 to 12 carbon atoms such as formic acid, acetic, propionic, butyric, isobutyric, valeric, caprioic, capric, perlargonic and lauric acids, together with dialiphatic acids of 2 to 6 carbons, such as oxalic, malonic, succinic and adipic acids. The invention further contemplates the use of substituted monoaliphatic acids containing one or more functional substituents, such as the lower alkoxy, chloro, fluoro, cyano, alkylthio, and amino functional groups, examples of which include acetoacetic acid, dichloroacetic and trifluroacetic acid, chloropropionic acid, trichloroacetic acid, monofluoroacetic acid and the like. Among the suitable aromatic acids contemplated are benzoic acid, naphthoic acids, toluic acids, chlorobenzoic acids, aminobenzoic acids and phenylacetic acid. The alicyclic monocarboxylic acids may contain from 3 to 6 carbons in the ring, both substituted and unsubstituted, and may contain one or more carboxyl groups, such as cyclopentanecarboxylic acid and hexahydrobenzoic acids. The heterocyclic acids may contain 1 to 3 fused rings both substituted and unsubstituted together with one or more carboxylic groups, examples include quinolinic, furoic and picolinic acids. Mixtures of said classes of carboxylic acids, in any ratio, may also be used in the inventive process. The preferred carboxylic acids are the lower aliphatic acids such as acetic acid, propionic acid and butyric acid, together with substituted aliphatic acids such as trifluoroacetic acid.

Also suitable in the practice of this invention are the acid anhydrides of said carboxylic acids. These acid anhydrides may be used both as useful solvents for the ruthenium catalyst and as coreactants which provide the acid moiety of the desired ethyl ester intermediate. Particularly useful are the anhydride of lower aliphatic carboxylic acids containing 3 to 12 carbon atoms such as acetic anhydride, propionic anhydride and n-butyric anhydride. Here reduction to practice includes Example 21.

C. Catalyst Concentration

The quantity of ruthenium catalyst employed in the instant invention is not critical and may vary over a wide range. In general, the novel process is desirably conducted in the presence of a catalytically effective quantity of the active ruthenium species which gives the desired ester products in reasonable yields. Reaction preceeds when employing as little as about $1 \times 10^{-6}$ weight percent, and even lesser amounts, of ruthenium, expressed as Ru basis the total weight of the reaction mixture. The upper concentration is dictated by a variety of factors including catalyst cost, partial pressures of carbon monoxide and hydrogen, operating temperature and choice of carboxylic acid diluent/reactant. A ruthenium catalyst concentration of from about $1 \times 10^{-5}$ to about 10 weight percent ruthenium, based on the total weight of reaction mixture, is generally desirable in the practice of this invention.

D. Operating Temperature

The temperature range which can usefully be employed in these ester syntheses is a variable dependent upon other experimental factors including the choice of carboxylic acid co-reactant, the pressure, and the concentration and particular choice of catalyst among other things. Again using ruthenium as the active metal, the range of operability is from about 100° to 350° C. when superatmospheric pressures of syngas are employed. A narrower range of 180°–260° C. represents the preferred temperature range when the major products are methyl and ethyl acetates. Table 2 is evidence of how the narrower range is derived.

E. Pressure

Superatmospheric pressures of 500 psi or greater lead to substantial yield of desirable alkanol ester by the process of this invention. A preferred operating range for solutions of ruthenium(IV) oxide in acetic acid is from 2000 psi to 7500 psi, although pressures above 7500 psi also provide useful yields of desired ester. Table 2 is evidence of this preferred, narrower range of operating pressures. The pressures referred to here represent the total pressure generated by all the reactants, although they are substantially due to the carbon monoxide and hydrogen fractions in these examples.

F. Gas Composition

The relative amounts of carbon monoxide and hydrogen which may be initially present in the syngas mixture are variable, and these amounts may be varied over a wide range. In general, the mole ratio of CO—to—$H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions such as carbon dioxide, hydrocarbons such as methane, ethane, propane and the like, ethers such as dimethyl ether, methylethyl ether and diethyl ether, alkanols such as methanol and acid esters such as methyl acetate.

In all syntheses, the amount of carbon monoxide and hydrogen present in the reaction mixture should be sufficient to satisfy the stoichiometry of eq (1).

G. Product Distribution

As far as can be determined, without limiting the invention thereby, the ruthenium-catalyst one-step CO-hydrogenation process disclosed herein leads to the formation of three classes of primary products, namely the methanol, ethanol and n-propanol ester derivatives of the corresponding co-reactant carboxylic acid. In the case then where propionic acid is the co-reactant, the principal products are methyl propionate, ethyl propionate and n-propyl propionate. Minor by-products detected in the liquid product fraction include small amounts of water, glycol dipropionate and n-butyl propionate. Carbon dioxide and methane may be detected in the off-gas together with unreacted carbon monoxide and hydrogen. Where >90% of the carboxylic acid charge has been converted to ester derivatives, the liquid product may also contain substantial quantities of methanol, ethanol and n-propanol.

H. Mode of Operation

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired ester product, and said material may be recovered by methods well known in the art, such as distillation, fractionation, extraction and the like. A fraction rich in ruthenium catalyst components may then be recycled to the reaction zone, if desired, and additional ester products generated by CO hydrogenation.

I. Identification Procedures

The products of CO-hydrogenation have been identified in this work by one or more of the following analytical procedures, viz, gas-liquid phase chromatography (glc), infrared (ir), mass spectrometry, nuclear magnetic resonance (nmr) and elemental analyses, or a combination of these techniques. Analyses have, for the most part, been by parts by weight, all temperatures are in degrees centigrade and all pressures in pounds per square inch gauge (psi).

PYROLYSIS OF ETHYL ESTERS

The pyrolytic elimination of esters may be carried out in either the liquid or the vapor phase by simply heating the ester in a metal bath, or with a free flame if its boiling point is sufficiently high, or by passing the compound through a heated tube. The ester pyrolysis reaction is relatively simple in experimental procedure, it does not require a catalyst, and yields are nearly always excellent, sometimes quantitative. Where the pyrolysis of an ester is carried out in the vapor phase, the ester is normally added dropwise to the top of a vertically-mounted quartz tube packed with glass helices or beads, the products are swept from the reaction chamber by a slow stream of inert gas and collected in suitable cold traps.

For preparative purposes the pyrolysis of aliphatic esters, particularly acyclic esters, to alkene and the corresponding acid is best carried out at temperatures ranging from 200° to 600° C. This temperature range is effective, for example, for the pyrolysis of ethyl esters of aliphatic carboxylic acids, where the desired products are ethylene and recovered carboxylic acid. Examples include the selective pyrolysis of ethyl propionate to ethylene and propionic acid, as well as the generation of ethylene plus acetic acid from ethyl acetate (eq 2).

Generally, these pyrolyses are most conveniently carried out at atmospheric or near-atmospheric pressures, in the presence of one or more inert gases used to sweep the product from the reaction zone. Suitable inert gases include helium, argon, neon, nitrogen and the like.

Having described the inventive process in general terms, the following examples are submitted to supply specific and illustrative embodiments.

SYNTHESIS OF ETHYL ESTERS

EXAMPLE I

To an 850 ml glass-lined autoclave reactor equipped for pressuring, heating, cooling and means of agitation is charged 0.764 gm of ruthenium(IV) oxide, hydrate (4.0 mmole), 17.64 gm of heptyl(triphenyl)phosphonium bromide (40 mmole) and propionic acid (50 gm). Upon stirring under a nitrogen atmosphere most of the solids dissolve to give a deep-red solution. The reactor is then sealed, flushed with $CO/H_2$, pressured to 2000 psi with synthesis gas (a 1:1 mixture of hydrogen and carbon monoxide) and heated to 220° C. with agitation. At temperature, the pressure within the reactor is raised to 6300 psi with $CO/H_2$ mix, and the pressure held constant throughout the 18 hour run by automatic addition of more synthesis gas from a large surge tank. Upon cooling, the excess gases are sampled and vented, and the deep-yellow liquid product (73.8 gm) removed for analysis. There is no solid product fraction.

Analysis of the liquid fraction by gas-liquid chromatography (glc) shows the presence of:

38.2 wt % ethyl propionate
16.5 wt % methyl propionate
8.4 wt % n-propyl propionate
0.8 wt % n-butyl propionate
0.9 wt % glycol dipropionate
2.7 wt % water
27.8 wt % unreacted propionic acid.

The ethyl propionate, together with the corresponding methyl, propyl and butyl propionates were isolated from a portion of the crude liquid product (58.8 gm) by stripping under reduced pressure (0.8 cm Hg). The residual liquid 'bottoms' (32.1 gm) contained the solubilized ruthenium catalyst, the clear distillate fraction (26.1 gm) contained:

58.3 wt % ethyl propionate
22.9 wt % methyl propionate
10.5 wt % propyl propionate
0.4 wt % butyl propionate This distillate liquid was further purified by fractional distillation.

EXAMPLE 2

To an 850 ml glass-lined autoclave equipped for pressurizing, heating, and means of agitation is charged 0.764 gm of ruthenium(IV) oxide, hydrate (4.0 mmole), 13.58 gm of tetrabutylphosphonium bromide (40 mmole), and 50 gm of propionic acid. The mixture is stirred to dissolve most of the solids, the reactor sealed, flushed with $CO/H_2$, pressured to 2000 psi with synthesis gas (1:1, $CO/H_2$) and heated to 220° C. with agitation. At temperature, the pressure within the reactor is raised to 6300 psi with $CO/H_2$ and the pressure held constant throughout the 18 hour run by automatic addition of more synthesis gas from a large surge tank. Upon cooling, the excess gases are sampled and vented, and the deep-red liquid product (87.8 gm) removed for analysis. There is no solid product fraction.

Analysis of the liquid fraction by gas-liquid chromatography (glc) shows the presence of:
31.8 wt % ethyl propionate
29.9 wt % methyl propionate
3.4 wt % n-propyl propionate
2.0 wt % n-butyl propionate
1.9 wt % propionic acid
14.3 wt % ethanol
7.5 wt % methanol
1.5 wt % n-propanol The ethyl propionate and ethanol, together with the corresponding $C_1$ and $C_3$–$C_4$ alkyl propionates, were isolated from the crude liquid product (50.3 gm) by fractional distillation under reduced pressure (0.4 cm Hg). The residual liquid 'bottoms' (12.5 gm) contained the solubilized ruthenium catalyst.

EXAMPLE 3

To an 850 ml glass-lined autoclave equipped for pressurizing, heating and means of agitation is charged 0.764 gm of ruthenium(IV) oxide, hydrate (4.0 mmole), 14.29 gm of methyl(triphenyl)phosphonium bromide (40 mmole) and propionic acid (50 gm). The mixture is stirred to dissolve most of the solids, the reactor sealed, flushed with $CO/H_2$ and pressured to 2000 psi with synthesis gas (1:1, $CO/H_2$). Over a period of 45–60 minutes the autoclave is heated, with agitation, to 220° C. At temperature the reactor pressure is raised to 6300 psi with $CO/H_2$ and the pressure held constant overnight by automatic addition of more synthesis gas from a large surge tank. Upon cooling, the excess gases are sampled and vented, and the deep-red liquid product (70.4 gm) removed for analysis. There is no solid product fraction.

Analysis of the liquid fraction by glc shows the presence of:
33.8 wt % ethyl propionate
32.6 wt % methyl propionate
7.2 wt % n-propyl propionate
0.7 wt % n-butyl propionate
0.99 wt % water
16.0 wt % unreacted propionic acid An analysis of a typical off-gas sample revealed the presence of:
38.8% hydrogen
38.2% carbon monoxide
12.8% carbon dioxide
6.2% methane.

Stripping of a sample of crude liquid product (59.0 gm) under reduced pressure (0.4 cm Hg) yielded a water-white distillate fraction (42.5 gm) and a red viscous liquid bottoms (15.7 gm) containing the active ruthenium catalyst. The distillate fraction showed the presence of:
35.2 wt % ethyl propionate
32.4 wt % methyl propionate
7.5 wt % propyl propionate Ethyl propionate may be isolated from this product distillate by fractional distillation.

EXAMPLES 4–11

Following the procedures of Example 1, in these examples synthesis gas conversion of ethyl propionate is carried out in the presence of a constant weight of ruthenium(IV) oxide, hydrate (4.0 mole) or ruthenium(IV) chloride, hydrate in combination with various quaternary alkyl and aryl ammonium and phosphonium halides, alkalimetal halides and iminium salts. A summary of the yield data for each of these ruthenium catalyst combinations is given in Table I.

Under standard screening conditions, the ruthenium(IV) oxide-heptyltriphenylphosphonium bromide catalyst system has proven to be the most selective catalyst. Ethyl propionate is obtained in 38 wt % concentration at 72% acid conversion (example 4). Selectively to ethyl ester is therefore 53% (basis liquid product).

The highest productivity has been achieved with the ruthenium(IV) oxide tetrabutylphosphonium bromide mix in propionic acid (example 5). Here propionic acid conversion is 98%, and the liquid weight gain is 24 gm (37%). Ethanol and ethyl propionate are obtained in 14.3 and 31.8 wt % concentrations, while the less desirable propanol+propyl propionate yields were down to 4.9 wt %. Three other ruthenium catalyst combinations of note, which generate ethyl propionate as the major product in good yields are:

$RuO_2$—$MePh_3PBr$, Example 6
$RuO_2$—$Ph_4PBr$, Example 7
and $Ru(acac)_3$-$HpPh_3PBr$, Example 13

More than a dozen ruthenium-quaternary Group VB salts have been evaluated for $CO/H_2$ conversion to ethyl propionate. The phosphonium "quats" have greater thermal stability than their ammonium congeners. Among the tetrabutylphosphonium and tetraphenylphosphonium quarternaries, the molar yield of $C_2$ ethyl ester/alcohol derivative varies for the catalyst series:

$Ru_{O2}$—$10Bu_4PX$ and $RuO_2$—$10Ph_4PX$ in the order:

Cl(36) < Br(273) > I(24)

and

Cl(13) < Br(98)

respectively. However, the desired ethyl propionate is the major product fraction only in the case of bromide salts.

In a similar comparison of various ruthenium(IV) oxide-quaternary Group VB salt combinations having the general formula:

$RuO_2$—$10R_4EBr$ the ethyl ester molar yield orders were found to follow the trends:

$Ph_4P(98) < Ph_3MeP(233) < Ph_3HpP(276) \sim Bu_4P(273)$ and $Bu_4N(21) < Bu_4P(273) > Cs(2)$ By contrast, ruthenium(IV) oxide alone, in the absence of any quaternary salt modifier, generates methyl propionate in 17% concentration as the major product, with only 0.2% desired ethyl propionate detected at 33% propionic acid conversion (example 21).

TABLE 1

Ethyl Propionate Synthesis from $CO/H_2$ - Ruthenium Catalyst Screening[a]

| Example | Ruthenium catalyst composition | Propionate esters | | | | | Alcohols | | | propionic acid | Off-gas composition, % | | | |
|---|---|---|---|---|---|---|---|---|---|---|---|---|---|---|
| | | Methyl | Ethyl | Propyl | Butyl | $H_2O$ | Methyl | Ethyl | Propyl | | $H_2$ | CO | $CO_2$ | $CH_4$ |
| 4 | $RuO_2$-10HpPh$_3$PBr | 16.5 | 38.2 | 8.4 | 0.8 | 1.2 | | | | 27.8 | 3.5 | 29.5 | 37.6 | 27.1 |
| 5 | $RuO_2$-10Bu$_4$PBr | 29.9 | 31.8 | 3.4 | 2.0 | 3.1 | 7.4 | 14.3 | 1.5 | 1.9 | 24.6 | 15.2 | 39.8 | 15.2 |
| 6 | $RuO_2$-10MePh$_3$PBr | 32.6 | 33.8 | 7.2 | 0.7 | 1.0 | | | | 16.0 | 38.8 | 38.2 | 12.8 | 6.2 |
| 7 | $RuO_2$-10Ph$_4$PBr | 14.7 | 14.8 | 17.0 | 1.3 | 0.6 | | | | 49.1 | 32.3 | 27.3 | 34.6 | 1.7 |
| 8 | $RuO_2$-10Ph$_4$PCl | 43.0 | 2.1 | 16.1 | 0.6 | 0.6 | | | | 34.2 | 38.9 | 30.8 | 25.8 | 1.8 |
| 9 | $RuO_2$-10Bu$_4$PCl | 44.6 | 5.1 | 13.9 | 1.1 | 4.0 | | | | 12.9 | 32.1 | 27.7 | 26.0 | 5.0 |
| 10 | $RuO_2$-10Bu$_4$PI | 2.7 | 3.8 | 5.2 | 1.2 | 0.6 | | | | 83.4 | 30.7 | 25.8 | 27.4 | 9.0 |
| 11 | $RuO_2$-10BzPh$_3$PBr | 10.2 | 5.0 | 16.7 | 1.7 | 0.5 | | | | 59.5 | 44.5 | 35.9 | 12.5 | 5.2 |
| 12 | $RuO_2$-10Bu$_4$POAc | 47.9 | 0.4 | 3.1 | | 0.5 | | | | 43.3 | 43.4 | 33.1 | 21.0 | 0.3 |
| 13 | Ru(acac)$_3$-10HpPh$_3$PBr | 32.5 | 33.8 | 10.4 | 0.7 | 1.2 | | | | 12.4 | 26.5 | 22.2 | 31.6 | 17.0 |
| 14 | $RuO_2$-10Me$_4$NBr | 53.1 | 10.7 | 10.0 | 2.7 | 1.0 | | | | 16.5 | 15.1 | 17.4 | 37.6 | 27.5 |
| 15 | $RuO_2$-10Bu$_4$NBr | 12.9 | 4.2 | 13.6 | 23.9 | 1.8 | | | | 36.7 | 9.6 | 3.6 | 66.3 | 15.0 |
| 16 | $RuO_2$-10PhMe$_3$NBr | 8.3 | 1.1 | 13.5 | 1.4 | 1.0 | | | | | 43.5 | 29.3 | 20.7 | 2.8 |
| 17 | $RuO_2$-10(Ph$_3$P)$_2$NBr | | | 0.3 | 0.4 | 2.2 | | | | 92.3 | 39.5 | 53.9 | 4.0 | 0.6 |
| 18 | $RuCl_3$-5(Ph$_3$P)$_2$NNO$_3$ | 48.2 | 14.2 | 9.6 | 1.8 | 2.9 | 6.4 | 3.2 | 3.5 | 3.7 | 19.8 | 20.6 | 33.3 | 12.7 |
| 19 | $RuO_2$-10CaI | 9.6 | 1.9 | 4.1 | | 5.5 | | | | 61.5 | 38.2 | 30.5 | 22.0 | 5.3 |
| 20 | $RuO_2$-10CaBr | 5.1 | 0.2 | 1.0 | 0.8 | 14.8 | | | | 66.0 | 19.6 | 15.6 | 42.5 | 4.4 |
| 21 | $RuO_3$ | 16.7 | 0.2 | 0.5 | 0.8 | 10.2 | | | | 66.6 | 49.4 | 42.5 | 6.3 | 0.2 |
| 22 | Ru(acac)$_3$[c] | 2.7 | | 0.3 | 0.1 | 1.0 | | | | 95.1 | 40.5 | 49.5 | 3.5 | 5.9 |

[a]Experimental conditions: Ru, 4.0 mmole, propionic acid, 50 gm; 220° C.; 6000-6300 psi, $CO/H_2$ (1:1).
[b]Estimated by glc; water by Karl-Fischer titration.
[c]Variable pressure run.

EXAMPLES 23-30

Following the procedure of Example 1, in these cases synthesis gas conversion of ethyl propionate is catalyzed by solution of ruthenium(IV) oxide, hydrate and heptyl(triphenyl) phosphonium bromide solubilized in propionic acid over a range of operating temperatures, pressures, ruthenium concentrations and quaternary phoshonium/Ru molar ratios. The yield data for each of these experimental ranges is summarized in Table 2.

Limiting experimental conditions for the ethyl propionate synthesis from $CO/H_2$ have been defined for a typical ruthenium-quaternary phosphonium salt catalyst [ruthenium(IV) oxide-heptyltriphenylphosphonium bromide] solubilized in propionic acid coreactant (see Table 2). Derived ethyl ester has been detected at a ruthenium concentration of 40-80 mM (millimeters) temperatures in the range 180°-260° C., and operating pressures down to 2000 psi. Maximum yields of ethyl propionate appear to be achieved, however, at operating temperatures around 220° C., pressures above 6000 psi and a [P]/[Ru] ratio of 4 (example 24). The principal by-products in the liquid fraction are consistently methyl and propyl propionate, $CO_2$ and methane continue to predominate in the gas phase.

EXAMPLE 31

To a 450 ml glass-lined autoclave equipped for pressuring, heating and means of agitation is charged 0.382 gm of ruthenium(IV) oxide, hydrate (2.0 mmole), 7.15 gm of methyl(triphenyl)phosphonium bromide (20 mmole) and 25 gm of acetic acid. The mixture is stirred to dissolve most of the solids, the reactor sealed, flushed with $CO/H_2$, pressured to 2000 psi with $CO/H_2$ (1:1) and heated to 220° with agitation. At temperature, the pressure within the reactor is raised to 6300 psi with $CO/H_2$ and the pressure held constant throughout the 18 hour run by automatic addition of more synthesis gas from a large surge tank. Upon cooling, the excess gases are sampled and vented, and the deep-red liquid product (33.5 gm) removed for analysis. There is no solid fraction.

Analysis of the liquid fraction by gas-liquid chromatography shows the presence of:
36.3 wt % ethyl acetate
21.9 wt % methyl acetate
2.5 wt % n-propyl acetate
3.2 wt % water
32.3 wt % unreacted acetic acid

TABLE 2

Synthesis of Esters of Propionic Acid from Syngas[a]

| Example | Ruthenium Catalyst Composition | Reaction | | Liquid Product Composition (wt %)[b] | | | | Unreacted Propionic Acid |
|---|---|---|---|---|---|---|---|---|
| | | Temp(°C.) | Pressure(psi) | Propionate Esters | | | $H_2O$ | |
| | | | | Methyl | Ethyl | Propyl | | |
| 23 | $RuO_2$-10HpPh$_3$PBr | 260 | 6300 | 72.0 | 2.7 | 7.5 | 1.2 | 3.3 |
| 24 | $RuO_2$-10HpPh$_3$PBr | 220 | 6300 | 16.5 | 38.2 | 8.4 | 1.2 | 27.8 |
| 25 | $RuO_2$-10HpPh$_3$PBr | 180 | 6300 | 16.4 | 3.3 | 2.4 | 0.15 | 75.5 |
| 26 | $RuO_2$-10HpPh$_3$PBr | 220 | 4000 | 12.2 | 12.4 | 17.5 | 0.59 | 54.0 |
| 27 | $RuO_2$-10HpPh$_3$PBr | 220 | 2000 | 4.3 | 0.5 | 25.2 | 0.50 | 66.6 |
| 28 | $RuO_2$-4HpPh$_3$PBr | 220 | 6300 | 21.1 | 32.5 | 9.4 | 1.10 | 29.3 |
| 29 | $RuO_2$-HpPh$_3$PBr | 220 | 6300 | 51.2 | 16.0 | 6.0 | 0.99 | 20.1 |
| 30 | $RuO_2$-10HpPh$_3$PBr[c] | 220 | 6300 | 24.8 | 24.6 | 10.0 | 0.76 | 36.3 |

[a]Experimental conditions: $RuO_2XH_2O$, 4.0 mmole; $C_2H_5COOH$, 50 gm.
[b]Estimated by gas-liquid chromatography, water by Karl-Fischer titration.
[c]Charging 2.0 mmole $RuO_2XH_2O$.

EXAMPLE 32

To a 300 ml glass-lined autoclave equipped for pressuring, heating and means of agitation is charged 0.40 gm of ruthenium(III) acetylacetonate (1.0 mmole), and 50 ml of acetic anhydride. The mixture is stirred under a nitrogen atmosphere to give a clear, deep-red solution. The reactor is then sealed, flushed with $CO/H_2$ (1:1) and pressured to 2700 psi with synthesis gas ($CO/H_2$1:1). Over a period of 60–75 minutes, the autoclave is heated, with agitation, to 220° C., and held at temperature overnight. Total gas uptake is 1150 psi. After cooling, the excess gases are vented and the deep-red liquid product (49 ml) removed for analysis. There is no solid fraction.

Analysis of this liquid product by glc shows the presence of:
30.1% ethyl acetate
0.5% methyl acetate
and 1.6% water.

EXAMPLES 33–38

Following the procedures of Example 21, in these cases synthesis gas conversion to ethyl acetate is carried out in the presence of a constant weight of ruthenium salt or complex (1–2 mmole) solubilized in acetic acid (50 ml). The yield data in Table 3 are illustrative of the use of ruthenium salts, such as ruthenium(III) chloride, hydrate and ruthenium(III) acetylacetonate in combination with tertiary group VB donar ligands such as triphenylphosphine and tri-n-butylphosphine, as well as of preformed ruthenium complexes such as dicarbonylbis(triphenylphosphine)ruthenium(II) chloride.

TABLE 3

Synthesis of Esters of Acetic Acid from Syngas[a]

| | | Liquid Product Composition (%)[b,c] | | | | |
|---|---|---|---|---|---|---|
| | Ruthenium Catalyst | Acetate Esters | | | | Unreacted |
| Example | Composition | Methyl | Ethyl | Propyl | $H_2O$ | Acetic Acid |
| 33 | $RuCl_2(PPh_3)_3$ | 0.5 | 3.8 | | 1.8 | 92.6 |
| 34 | $RuCl_2(CO)_2(PPh_3)_2$ | 0.4 | 4.1 | | 1.6 | 93.5 |
| 35 | $Ru(acac)_3$-$2PBu_3$ | 3.6 | 6.4 | | 1.3 | 87.6 |
| 36 | $RuCl_3$-$3PBu_3$ | 0.2 | 6.7 | | 3.2 | 89.5 |
| 37 | $RuCl_3$-$3P(OPh)_3$ | 4.4 | 19.5 | | 4.0 | 65.7 |
| 38 | $RuCl_3$-$3AsMe_3$ | 0.6 | 8.4 | | 4.0 | 83.3 |

[a]Experimental conditions
[b]Estimated by gas-liquid chromatography, water by Karl-Fischer titration
[c]Includes some ethyl acetate generated via acetic acid reduction

EXAMPLES 39–47

Some dozen other late transition-metal salts and carbonyls from Groups VI–VIII have been screened as homogeneous catalysts for $CO/H_2$ conversion to ethyl propionate (eg. 1), usually in combination with typical quaternary phosphonium salts. The results, summarized in Table 4, show only rhodium(III) acetylacetonate-tetrabutylphosphonium bromide example 40 and rhenium decacarbonyl-tetrabutylphosphonium acetate (example 45) yield significant quantities of desired ethyl ester under our selected screening conditions. Furthermore, in both these cases, the predominent ester product is propyl propionate.

The positive data of examples 1–38 in conjunction with the negative data of examples 39–47 emphasize the specific activity of the ruthenium Group VB ligand catalysts for the synthesis of ethyl esters of acrylic carboxylic acids.

Particularly the data in Example 40 table 4 which show only 0.5% of ethyl propionate in the liquid product from rhodium III acetylacetonate pentatributylphosphonium bromide catalyst are contrasted with data of Example 13 which show 33.8% ethyl propionate in the liquid product from ruthenium III acetyl acetonate-deca [heptyl triphenyl phosphonium bromide] catalyst. Clearly ruthenium is a specific catalyst for the synthesis of ethyl esters.

TABLE 4

Ethyl Propionate Synthesis from $CO/H_2$ - Metal Catalyst Screening[a]

| | | Liquid product composition, wt %[b] | | | | | |
|---|---|---|---|---|---|---|---|
| | Ruthenium catalyst | Propionate esters | | | | | Unreacted propionic |
| Example | composition | Methyl | Ethyl | Propyl | Butyl | $H_2O$ | acid |
| 39 | $Co_2(CO)_8$-$5Bu_4PBr$ | 1.4 | | 6.5 | 1.7 | 3.0 | 84.0 |
| 40 | $Rh(acac)_3$-$5Bu_4PBr$ | 1.2 | 0.5 | 6.4 | 0.1 | 0.3 | 87.9 |
| 41 | $Fe_2O_3$-$10HpPh_3PBr$ | | | 0.2 | | 0.5 | 98.8 |
| 42 | $Ni(OAc)_2$-$5Bu_4PBr$ | | | 0.3 | | 1.0 | 98.5 |
| 43 | $Mn_2(CO)_{10}$-$5Bu_4PBr$ | | | | | 0.3 | 99.8 |
| 44 | $Re_2(CO)_{10}$-$5Bu_4PBr$ | | | 8.5 | | 0.3 | 90.6 |
| 45 | $Re_2(CO)_{10}$-$5Bu_4POAc$ | 13.5 | 2.1 | 37.6 | | 4.6 | 38.2 |
| 46 | $Cr(acac)_3$-$5Bu_4PBr$ | 0.2 | | | | 0.1 | 99.2 |
| 47 | $Mo(acac)_3$-$5Bu_4PBr$ | | | 0.2 | | 0.6 | 98.8 |

[a]Run conditions: metal, 2 mmole; propionic acid, 25 gm; 220° C.; ca. 6300 psi, 18 hr.
[b]Estimated by glc, water by Karl-Fischer titration.

EXAMPLES 48–52

Multiple cycling of two ruthenium catalyst formulations has been demonstrated in two series of batch studies using the 845 ml capacity reactor. For the ruthenium(III) acetylacetonate-heptyltriphenylphosphonium bromide formulation, the crude liquid product is a deep-red liquid (75.0 gm) with no solid precipitate 48) this liquid fraction (65.6 gm) is subject to fractional distillation under reduced pressure (1 mm Hg) and pot temperatures to 45° C. The clear, water-white distillate fractions are set aside for analysis, glc-trapping etc. The deep-red liquid residue (25.2 gm) is recycled to the batch reactor with additional propionic acid (50 gm) and CO/H$_2$ (1:1). CO-Hydrogenation is repeated and the crude product fractionally distilled as described supra.

The ruthenium(III) acetylacetonate-heptyltriphenylphosphonium bromide combination shows good activity over three cycles (Table 5).

CO/H$_2$) and heated to 220° C. with agitation. At temperature, the pressure within the reactor is raised to 6300 psi with CO/H$_2$ addition, and the pressure held constant throughout the 18 hour run by automatic addition of more synthesis gas from a large surge tank. Upon cooling, the excess gases are sampled and vented, and the deep-red liquid product (87.8 gm) removed for analysis. There is no solid product fraction.

TABLE 5

Ethyl Propionate Synthesis from CO/H$_2$ - Ruthenium Catalyst Recycle[a]

| Catalyst cycle | Example | Ruthenium catalyst composition | Liquid product composition (wt %)[b] | | | | | |
|---|---|---|---|---|---|---|---|---|
| | | | Propionate esters | | | | | propionic |
| | | | Methyl | Ethyl | Propyl | Butyl | H$_2$O | acid |
| 1 | 48 | Ru(acac)$_3$-10HpPh$_3$PBr | 32.5 | 33.8 | 10.5 | 0.7 | 1.2 | 12.4 |
| | | Distillate Cut #1 | 40.6 | 43.1 | 8.6 | 0.5 | 1.3 | 1.8 |
| | | Distillate Cut #2 | 11.7 | 33.6 | 16.1 | 1.1 | 1.2 | 4.7 |
| 2 | 49 | Ex. 48 Residue - charge | | | 0.1 | | | 97.9 |
| | | Ex. 48 Residue - product | 25.0 | 14.0 | 13.9 | 0.7 | 1.0 | 42.5 |
| | | Distillate Cut #1 | 41.5 | 17.3 | 15.8 | 1.0 | 0.5 | 22.3 |
| 3 | 50 | Ex. 49 Residue - charge | | | 0.1 | | 1.9 | 96.7 |
| | | Ex. 49 Residue - product | 41.7 | 15.6 | 13.1 | 1.0 | 0.4 | 25.8 |
| 1 | 51 | RuO$_2$-10MePh$_3$PBr | 32.6 | 33.8 | 7.2 | 0.7 | 1.0 | 16.0 |
| | | Distillate Cut #1 | 32.4 | 35.2 | 7.5 | 0.8 | 2.4 | 16.6 |
| 2 | 52 | Ex. 57 Residue - charge | | | | | | |
| | | Ex. 57 Residue - product | 25.3 | 14.3 | 14.7 | 0.8 | 0.6 | 41.7 |

[a]Experimental conditions: Ru, 4.0 mmole; propionic acid, 50 gm; 220° C., ca. 6300 psi, 18 hr.
[b]Data estimated by glc.

EXAMPLE 53

To an 850 ml glass-lined autoclave equipped for pressurizing, heating, and means for agitation is charged 0.764 gm of ruthenium(IV) oxide, hydrate (4.0 mmole), 13.58 gm of tetrabutylphosphonium bromide (40 mmole), and 50 gm of n-butyric acid. The mixture is stirred to dissolve most of the solids, the reactor sealed, flushed with CO/H$_2$, pressured to 2000 psi with synthesis gas (1:1, CO/H$_2$) and heated to 220° C. with agitation. At temperature, the pressure within the reactor is raised to 6300 psi with CO/H$_2$ and the pressure held constant throughout the 18 hour run by automatic addition of more synthesis gas from a large surge tank. Upon cooling, the excess gases are sampled and vented, and the deep-red liquid product (87.8 gm) removed for analysis. There is no solid product fraction.

Analysis of the liquid fraction by gas-liquid chromatography (glc) shows the presence of:
31.8 wt % ethyl butyrate
29.9% wt % methyl butyrate
3.4 wt % n-propyl butyrate
2.0 wt % n-butyl butyrate
1.9 wt % butyric acid
14.3 wt % ethanol
7.5 wt % methanol
1.5 wt % n-propanol The ethyl butyrate and ethanol, together with the corresponding C$_1$ and C$_3$-C$_4$ alkyl butyrates, are isolated from the crude liquid product (50.3 gm) by fractional distillation under reduced pressure (0.4 cm Hg). The residual liquid 'bottoms' (12½ gm) contained the solubilized ruthenium catalyst.

EXAMPLE 54

To an 850 ml glass-lined autoclave equipped for pressurizing, heating and means of agitation is charged 0.764 gm of ruthenium(IV) oxide, hydrate (4.0 mmole), 13.58 gm of tetrabutylphosphonium bromide (40 mmole), and 50 gm of tricluoxacitic acid. The mixture is stirred to dissolve most of the solids, the reactor sealed, flushed with CO/H$_2$, pressured to 2000 psi synthesis gas (1:1, Analysis of the liquid fraction by gas-liquid chromatography (glc) shown the presence of:
31.8 wt % ethyl trifluoracetate
29.9 wt % methyl trifluoracetate
3.4 wt % n-propyl trifluoracetate
2.0 wt % n-butyl trifluoracetate
1.9 wt % trifluoracetic acid
14.3 wt % ethanol
7.5 wt % methanol
1.5 wt % n-propanol The ethyl trifluoracetate and ethanol, together with the corresponding C$_1$ and C$_3$-C$_4$ alkyl proponates, were isolated from the crude liquid product (50.3 gm) by fractional distillation under reduced pressure (0.4 cm Hg). The residual liquid 'bottoms' (12½ gm) contained the solubilized ruthenium catalyst.

PYROLYSIS OF ETHYL ESTER

EXAMPLE 55

A 3.5 cm diameter quartz tube, 43 cm in length, is packed with glass helices, set in a vertical plane and heated to 450°-460° C. Helium is passed slow through the tube at a rate of 60 ml/min, and ethyl propionate is added dropwise to the top of the packed bed at a rate of 1-2 ml/min. The effluent gases pass first through an air trap and then through two further traps cooled in dry-ice-acetone (trap 2) and a liquid nitrogen-n-propanol slush bath (trap 3). After one hour of operation, an analysis of the water-white liquid (48.8 gm) in trap 1 showed the presence of:
34.9% propionic acid
64.1% ethyl propionate
0.1% methyl propionate.

The liquid collected in trap 3 showed the presence of:
92% ethylene
4% ethane.

EXAMPLE 56

Using the quartz tube and procedures of Example 28, ethyl acetate is added dropwise to the top of the helix bed at a rate of 1–2 ml/min. After 90 minutes, an analysis of the water-white liquid (58 ml) in trap 1 showed the presence of:
54.1% acetic acid
43.3% ethyl acetate
1.7% water.

The liquid collected in trap 3 showed the presence of:
71% ethylene
6% methyl acetate
21% ethyl acetate.

EXAMPLE 57

Using the apparatus and pyrolysis procedures of Example 28, a sample (20.6 gm) of the clear, distillate liquid product from Example 1 is added dropwise to the top of the helix bed of the pyrolysis reactor at a rate of 1–2 ml/min. The bed temperature is 450°–460° C. The effluent gases are passed first through the air trap and then through two further traps cooled in dry-ice-acetone (trap 2) and a liquid nitrogen-n-propanol slush bath (trap 3). After 30 minutes of operation, an analysis of the water-white liquid (15.5 gm) in trap 1 showed the presence of:
33.9 wt % propionic acid
24.9 wt % methyl propionate
27.2 wt % ethyl propionate
6.2 wt % propyl propionate The liquid collected in trap 3 showed the presence of:
54% ethylene
6% ethane.

As the examples and preceeding discussion have documented, numerous advantages accure from the practice of this invention both in its compositional and process aspects. For example, a relatively large group of ruthenium catalyst combinations are disclosed herein which are useful for the one-step conversion of synthesis gas to ethyl ester derivatives of carboxylic acids. Furthermore, it is disclosed that the activity of the ruthenium catalysts is significantly improved through the addition of certain classes of coordinating ligands and cocatalyst species, particularly the presence of large cationic species. In the presence of said classes of ruthenium catalyst, selective syntheses of desired products has been demonstrated.

Furthermore, in this invention is disclosed a relatively simply, but novel, two-step synthesis of ethylene from synthesis gas employing said classes of ruthenium catalyst for the selective synthesis of said ethyl esters of carboxylic acids, which are then isolated and pyrolyzed to yield the desired ethylene product and regenerate the starting carboxylic acid.

Finally, the invention is advantageous in that numerous substitutions, modifications and changes can be made without departing from the inventive concept. However, the scope of the subject invention may best be understood by examining the claims, which follow, read in conjunction with the preceeding specification.

What is claimed is:

1. A process for the synthesis of ethylene from mixtures of carbon monoxide and hydrogen which comprises the following steps:

(1) Contacting a mixture of carbon monoxide and hydrogen with one or more $C_2$–$C_4$ aliphatic carboxylic acids, the corresponding acid anhydrides, trifluoroacetic acid or the corresponding anhydride, and a ruthenium catalyst selected from the group consisting of ruthenium (IV) dioxide hydrate, ruthenium (VIII) tetraoxide, ruthenium acetate, ruthenium propionate, ruthenium acetyl acetonate, ruthenium chloride and ruthenium bromide, and a cocatalyst selected from the group consisting of cesium salts, quaternary ammonium and phosphonium salts and iminium salts, to form a reaction mixture;

(2) Heating said reaction mixture to temperatures between about 100° and 350° C., at superatmospheric pressures of 500 psi or greater to effect formation of predominantly the methyl, ethyl and propyl esters of said carboxylic acids, (3) Isolating said formed ethyl ester and pyrolyzing said isolated formed ester under an inert atmosphere to yield ethylene and also regenerating the carboxylic acid coreactant.

2. The process of claim 1 wherein the ruthenium catalyst is ruthenium acetate or ruthenium acetyl acetonate.

3. The process of claim 1 wherein the ruthenium chloride is selected from the group consisting of ruthenium chloride hydrate and anhydrous ruthenium chloride.

4. The process of claim 1 wherein the ruthenium catalyst contains one or more Group VA tertiary donor ligands.

5. The process of claim 4 wherein the Group VA tertiary donor ligands are selected from the group consisting of triphenylphosphine, tri-n-butylphosphine, triphenylphosphite, triethylphosphite, trimethylphosphine, triphenylarsine and trimethylarsine.

6. The process of claim 1 wherein the cesium salt is selected from the group consisting of cesium bromide, cesium iodide and cessium acetate.

7. The process of claim 1 wherein the cocatalyst is a quaternary ammonium or phosphonium salt.

8. The process of claim 7 wherein the quaternary phosphonium salt cocatalyst is a quaternary phosphonium salt of a mineral acid.

9. The process of claim 8 wherein the quaternary phosphonium salt cocatalyst is selected from the group consisting of heptyl(triphenyl)-phosphonium bromide, tetrabutylphosphonium bromide, methyl(triphenyl)-phosphonium bromide, tetraphenylphosphonium bromide, tetrabutylphosphonium chloride, and tetrabutylphosphonium iodide.

10. The process of claim 1 wherein the cocatalyst is an iminium salt.

11. The process of claim 10 wherein the iminium salt cocatalyst is selected from the group consisting of bis(triphenylphosphine)iminium acetate and bis(triphenylphosphine)iminium nitrate.

12. The process of claim 7 wherein the quaternary ammonium salt cocatalyst is a quaternary ammonium salt of a mineral acid.

* * * * *